United States Patent [19]

Lehky

[11] 4,414,418
[45] Nov. 8, 1983

[54] PROCESS FOR THE PRODUCTION OF DIMEDONE

[75] Inventor: Pavel Lehky, Naters, Switzerland

[73] Assignee: Lonza Ltd., Gampel, Switzerland

[21] Appl. No.: 379,718

[22] Filed: May 19, 1982

[30] Foreign Application Priority Data

May 27, 1981 [CH] Switzerland .................. 3473/81

[51] Int. Cl.³ ............................................. C07C 45/48
[52] U.S. Cl. .................................... 568/346; 560/174; 562/577; 549/546; 568/377
[58] Field of Search .................. 568/346; 560/174; 562/577

[56] References Cited

U.S. PATENT DOCUMENTS

| | | | |
|---|---|---|---|
| 2,917,537 | 12/1959 | Haury | 560/174 |
| 2,944,899 | 7/1960 | Damschroder et al. | 96/95 |
| 3,349,130 | 10/1967 | Bucourt et al. | 568/346 |
| 3,775,435 | 11/1973 | Sellstedt et al. | 260/345.2 |
| 3,823,164 | 7/1974 | Sellstedt et al. | 260/343.2 |
| 3,932,511 | 1/1976 | Schaafsma et al. | 568/346 |
| 3,976,785 | 8/1976 | Diehl et al. | 424/324 |
| 4,028,417 | 6/1977 | Muller et al. | 568/346 |

FOREIGN PATENT DOCUMENTS 2201668 10/1972 Fed. Rep. of Germany .
2512586 10/1975 Fed. Rep. of Germany .
7747949 of 0000 Japan .
7833143 of 0000 Japan .

OTHER PUBLICATIONS

Chavdorian et al., Chem. Abst., vol. 83, #179317X, (1975).
R. Semet et al., Bull. Chim. Soc., France (1978), (3–4), II, p. 185.
T. Henshall et al., J. Amer. Chem. Soc., 77, (1955), p. 6656.
Organic Syntheses, Coll. II, (1943), p. 200.
G. B. Payne, J. Org. Chem. 24, (1959), p. 719.
M. Quadrat-I-Khuda, J. Chem. Soc., (1929), p. 201.

*Primary Examiner*—James H. Reamer
*Attorney, Agent, or Firm*—Fisher, Christen & Sabol

[57] ABSTRACT

Process for the production of dimedone from isophorone. The isophorone is converted in the presence of a solvent with ozone into an ozone-addition product. An alcohol corresponding to the ester radical is added at the latest after the formation of the ozone-addition product for the formation of the intermediate product, 3,3-dimethyl-5-oxo-hexanoic acid ester. The ozone addition product is heated in the presence of acids to a temperature of 20° to 150° C. The 3,3-dimethyl-5-oxo-hexanoic acid ester is isolated thereby. The ester is then converted in a further step into dimedone by treatment of the ester with an alkali alcoholate in an anhydrous milieu.

16 Claims, No Drawings

PROCESS FOR THE PRODUCTION OF DIMEDONE

BACKGROUND OF THE INVENTION

1. Field of the Invention

The invention relates to a process for the production of dimedone from isophorone.

2. Prior Art

Dimedone has various uses as an intermediate product in the chemical industry, such as, in the production of pharmaceuticals (U.S. Pat. Nos. 3,775,435 and 3,823,164), herbicides or pesticides (German OS No. 22 01 668 and U.S. Pat. No. 3,976,785) and polymerizates (Japanese Pat. No. 77 47949), in photochemistry (U.S. Pat. No. 2,944,899 and Japanese Pat. No. 78 33143) and in analyticals (German OS No. 25 12 586).

Various methods for the production of dimedone are known in the literature. In *Organic Synthesis,* Coll. II, 200 (1943), a process is mentioned which starts out from malonic ester and mesitylic oxide. T. Henshall et al. J. Amer. Chem. Soc. 77, 6656 (1955), obtained dimedone by the cyclization of 3,3-dimethyl-5-oxo-hexanoic acid with sulphuric acid. G. B. Payne, J. Org. Chem. 24, 719 (1959), produces dimedone from isophorone with the help of a multistage, complicated process:

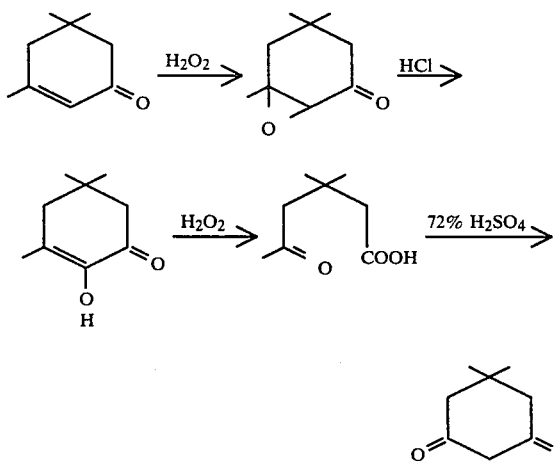

All these processes have various disadvantages, such as, low yields, poor accessability to the 3,3-dimethyl-5-oxo-hexanoic acid, and large amounts of organic waste, but particularly in the latter case, many individual reaction steps.

BROAD DESCRIPTION OF THE INVENTION

The main object of the invention is to provide a process, starting out with an inexpensive educt, to produce high purity dimedone in a simple manner without the need of using additional, expensive purifying processes. Other objects and advantages of this invention are set out herein or are obvious herefrom to one ordinarily skilled in the art.

The objects and advantages of the invention are achieved by the process of the invention.

This invention involves a process for the production of dimedone. The process starts out by converting isophorone, dissolved in a solvent, with ozone into an ozone-addition product. The ozone-addition product is changed with the help of an alcohol added at the latest after formation of the ozone-addition product and of a strong acid into 3,3-dimethyl-5-oxo-hexanoic acid ester, an intermediate product. After isolation, the latter is reacted in a second step by the addition of an alkali metal alcoholate to produce the desired dimedone.

The reaction of the invention can be carried out discontinuously or continuously in the first step.

The first part of the first step is carried out in the presence of at least one solvent. Such solvents can be alcohols, which correspond to the ester radical of the 3,3-dimethyl-5-oxo-hexanoic acid ester, or can be solvents such as hydrocarbons, halogenated hydrocarbons, esters such as acetic ester, and others. Examples of useful alcohols are those having one to six carbon atoms, such as, methanol, ethanol, pentanol, hexanol, butanol, isopropanol and propanol. Examples of useful hydrocarbons are hexane and pentane. Examples of useful halogenated hydrocarbons are dichloroethane, trichloroethane, difluorobutane, dibromoethane and dichloropropane. Whenever the non-alcohol solvents are used, then it is necessary to add the alcohol after formation of the ozone-addition product, in order to achieve an alcoholysis of the ozone-addition product into the ester.

Isophorone can also be reacted with ozone without the presence of any solvent. In the case of this method of operation, one should pay attention for reasons of safety that only 20 to 30 percent of the isophorone used is converted into an ozone-addition product. In this case too, the alcoholysis of the ozone-addition product is accomplished by the addition of an alcohol.

Preferably alcohols, which correspond to the ester radical of the 3,3-dimethyl-5-oxo-hexanoic acid ester, are used as the solvents.

The ozonolysis can be carried out effectively at a temperature of $-80°$ to $+50°$ C., with the preferred range being between $-10°$ to $+30°$ C.

The duration of the ozonolysis depends mainly on the capacity of the ozone generator and can lie between a few minutes and hours. Medium reaction times lie at about 0.5 to 5 hours.

The concentration of the isophorone in the solvent is only of secondary importance. It only has a small influence on the yields and preferably lies between 5 and 35 percent.

The duration of the after treatment, i.e., the esterification, of the ozone-addition product depends upon the temperature and lies between 0.5 to 25 hours. Effectively one operates at a temperature of 20° to 150° C., whereby the medium reaction time amounts to 3 hours.

Advantageously sulfuric acid, hydrochloric acid and acid ion exchangers are useful as the strong acids.

The isolation of the 3,3-dimethyl-5-oxo-hexanoic acid ester can be carried out according to known methods such as distillation, extraction, etc.

In the second step, i.e., in the case of the conversion of the isolated ester into dimedone, one preferably procceds as follows: A sodium alcoholate solution in alcohol is put into a suitable container, equipped with a stirrer, a reflux cooler and a dripping apparatus. This solution preferably contains 1.2 to 1.5 equivalents of alkali metal alcoholate, related to the amount of 3,3-dimethyl-5-oxo-hexanoic acid ester, but dimedone is also formed with the use of lower or higher quantities of alkali metal alcoholate. Examples of the alkali metal alcoholates are sodium ethylate, sodium methylate, potassium propylate, lithium butylate, potassium ethylate and potassium methylate—preferably the alcohol residue has one to four carbon atoms. The ester is added slowly, drop by drop, to the alkali metal alcoholate solution; the entire mixture is kept for 1 to 2 hours at reflux temperature; and the mixture is then mixed with water and acidified with a strong acid. Advantageously sulfuric acid or hydrochloric acid is used as the strong acid and the acidification is carried out until a pH of about 2 is achieved. After acidification, the alcohol is distilled off and the remaining aqueous solution is cooled. At the same time the dimedone crystallizes out as a colorless substance.

By way of summary, dimedone is obtained from isophorone, by way of its ozone-addition product, the 3,3-dimethyl-5-oxo-hexanoic acid ester made from it, and after treatment of the latter with a stoichiometric quantity of a sodium alcoholate.

DETAILED DESCRIPTION OF THE INVENTION

As used herein, all parts, ratios, proportions and percentages are on a weight basis unless otherwise stated herein or otherwise obvious herefrom to one ordinarily skilled in the art.

EXAMPLE 1

1st Step

A solution of 200 g of isophorone in 1500 g of methanol was continuously introduced over a 20 hour period from the top into a bell bottom column. Oxygen, which contained about 4 percent of ozone was fed-in from below. The fluid phase and the gaseous phase thus moved in counter current. The column was cooled on the outside by a cooling jacket to 0° to 2° C. The solution, which continuously ran out of the column on the bottom was mixed with 6.4 g of concentrated sulfuric acid and was heated up for a refluxing step. After the ozonolysis was completed, the reaction solution was boiled under reflux for 3 hours. Subsequently the entire mix was cooled down to 20° C. and neutralized with sodium hydroxide dissolved in methanol. The methyl alcohol was distilled off under normal pressure. The ester formed was isolated by vacuum distillation (boiling point: 80° to 82° C. at 14 mbar).

231.4 g of a colorless to lightly yellow fluid was obtained which (according to gas chromatography) contained 98.1 percent of 3,3-dimethyl-5-oxo-hexanoic acid methyl ester. This corresponded to 227.0 g of 100 percent ester and to a yield of 91.1 percent, calculated on the amount of isophorone used.

2nd Step

In a round bottom flask equipped with stirrer, reflux cooler, $CaCl_2$-pipe and a pot-shaped funnel, 4.8 g of metallic sodium was dissolved in 60 $cm^3$ of methanol and everything was heated up to reflux temperature. Then 30.0 g of the 98.1 percent 3,3-dimethyl-5-oxo-hexanoic acid methyl ester, obtained from the first step, was slowly added drop by drop and the solution was further treated during a 2 hour period at reflux temperature. After cooling to 25° C. the solution was treated with 150 ml of $H_2O$ and adjusted with concentrated hydrochloric acid to a pH value of about 2. The methanol was distilled off under normal pressure by way of a Claisen attachment. The residue was subsequently cooled to 10° C. At the same time dimedone was obtained in the form of colorless crystals. The product was filtered off, washed on the suction filter with a little water, and dried at 40° C. at 20 mbar.

21.07 g of dimedone, having a melting point of 147° to 148° C., was obtained. The dimedone according to potentrometric titration had a content of 98.2 percent, which corresponds to 20.69 g of 100 dimedone and which corresponds to a yield of 86.4 percent, calculated on the amount of ester used, or of 78.7 percent calculated on the amount isophorone used.

Another 1.85 g of dimedone was found in the mother lye (with gas chromatography). The quantity of dimedone formed altogether thus amounted to 22.54 g, which corresponds to a 94.1 percent yield, related to the amount of ester used, or a 85.7 percent yield, related to the amount of isophorone used.

EXAMPLE 2

A solution of 15.8 g of isophorone in 55.0 g of methanol was ozonolized at −2° to 0° C. for 2 hours. After addition of 0.91 g of concentrated sulfuric acid, the reaction solution was cooked under reflux for 16 hours. The pH of the solution was adjusted with an $N_2$ methanolic solution of sodium hydroxide to pH 7 and the methanol was distilled off. The ester formed was isolated by vacuum distillation.

17.2 g of a lightly yellow fluid (boiling point: 80° to 82° C. at 14 mbar) was obtained which according to gas chromatography contained 97.2 percent of 3,3-dimethyl-5-oxo-hexanoic acid methyl ester. This corresponds to 16.7 g of 100 percent ester and to a yield of 84.8 percent, calculated on the amount of isophorone used.

EXAMPLE 3

A solution of 15.8 g of isophorone in 70.0 g of ethylacetate was ozonolized at 0° C. for 2 hours. After addition of 80.0 g of absolute ethanol and 0.91 g of concentrated sulfuric acid, the reaction solution was cooked overnight under reflux. The cooled solution was adjusted to pH 7 with an ethanolic solution of sodium hydroxide. The ethanol and the ethylacetate were distilled off. The desired 3,3-dimethyl-5-oxo-hexanoic acid ethyl ester was isolated by vacuum distillation. 18.6 g of a colorless fluid (boiling point: 104° to 105° C. at 19 mbar) was obtained which according to gas chromatography contained 98.2 percent of 3,3-dimethyl-5-oxohexanoic acid ethyl ester. This corresponds to 18.3 g of 100 percent ester and to a yield of 85.9 percent, calculated on the amount of isophorone used.

EXAMPLE 4

In an apparatus, consisting of a round column, a reflux cooler with chlorcalcium pipe and a drip funnel, 3.8 g of solid sodium methylate were heated in 20 ml of dry dimethyl sulfoxide to 80° to 100° C. Within 10 minutes 10.215 g (93.3 mole) of 3,3-dimethyl-5-oxo-hexanoic acid methyl ester, which had been produced as in one of the preceding examples, was allowed to flow in drop by drop. The solution was digested during a 2 hour period while maintaining the stated temperature, then it was cooled to ambient temperature and mixed with 80 ml of water. This solution was adjusted with concentrated hydrochloric acid to pH 2. At the same time the product was obtained as a colorless crystal paste which was filtered out using a suction filter. The product was washed with a little water and dried in a vacuum drier at 40° C.

6.622 g of dimedone at a purity of 98.6 percent was obtained, which corresponds to 6.52 of 100 percent dimedone, and which corresponds to a yield of 78.5 percent, related to the amount of 3,3-dimethyl-5-oxo-hexanoic-methyl ester used.

EXAMPLE 5

In a 100 ml round column having a reflux cooler, a chlorcalcium pipe and a drip funnel, 3.7 g of solid sodium methylate was heated in 20 ml of dry acetonitrile to the reflux temperature. 9.873 g (0.057 mole) of 3,3-dimethyl-5-oxo-hexanoic acid methyl ester, which was produced as in a preceding example, was added drop by drop within a 10 minute period and subsequently left during a 2 hour period under reflux. The reaction mixture obtained was reduced on a rotation evaporator. The evaporation residue was dissolved in 60 ml of water and was adjusted with concentrated hydrochloric acid to pH 2. The precipitated dimedone was filtered off, washed on the suction filter with a little water and dried at 40° C. in a vacuum drier.

6.728 g of dimedone was obtained as colorless crystals having a purity of 98.8 percent (potentiometric titration). This corresponds to 6.647 g of 100 percent product, and corresponds to a yield of 83.2 percent, related to the amount of 3,3-dimethyl-5-oxo-hexanoic acid methyl ester.

What is claimed is:

1. Process for the production of dimedone from isophorone, comprising converting isophorone in a solvent present in an amount sufficient to act as a solvent with ozone present in an amount sufficient to effect the isophorone-conversion into an ozone-addition product, said solvent being a hydrocarbon a halogenated hydrocarbon, an ester solvent or an alcohol having 1 to 6 carbon atoms, heating the ozone-addition product in the presence of an acid which is present in an effective amount to a temperature of 20° to 150° C., adding an alcohol at the latest after the formation of the ozone-addition product when the solvent is a non-alcohol solvent whereby the intermediate product 3,3-dimethyl-5-oxo-hexanoic acid ester forms, the alcohol being present in an amount sufficient to form said ester, the alcohol corresponding to the ester radical, isolating the 3,3-dimethyl-5-oxo-hexonic acid ester, and converting said ester by treatment with an alkali alcoholate present in an amount sufficient to effect the ester-conversion in an anhydrous milieu into dimedone.

2. Process as claimed in claim 1 wherein the ester moiety has 1 to 6 carbon atoms.

3. Process as claimed in claim 1 wherein the alcohol is methanol, ethanol, pentanol, hexanol, butanol, isopropanol or propanol, the ester solvent is acetic ester, the hydrocarbon is hexane or pentane and the halogenated hydrocarbon is dichlorethane, trichloroethane, difluorobutane, dibromoethane or dichloropropane.

4. Process as claimed in claim 1 wherein the acid is sulfuric acid, hydrochloric acid or an acid ion exchanger.

5. Process as claimed in claim 1 wherein the alkali acoholate is sodium ethylate, sodium methylate, potassium propylate, lithium butylate, potassium ethylate or potassium methylate.

6. Process as claimed in claim 1 wherein the alkali alcoholate has an alcohol residue which has 1 to 4 carbon atoms.

7. Process as claimed in claim 1 wherein an alcohol, which corresponds to the ester radical, is used as the solvent and is added to the reaction mix prior to the formation of the ozone-addition product.

8. Process as claimed in claim 1 wherein the first step is carried out on a continuous basis.

9. Process as claimed in claim 1 wherein the ozonolysis is carried out at a temperature of −80° to +50° C.

10. Process as claimed in claim 1 wherein the concentration of the isophorone in the solvent is between 2 and 100 percent.

11. Process as claimed in claim 1 wherein the concentration of the isophorone in the solvent is between 3 and 35 percent.

12. Process as claimed in claim 1 wherein an alcohol, which corresponds to the ester radical, is used as the solvent and is added to the reaction mix prior to the formation of the ozone-addition product, the first step is carried out continuously, the ozonolysis is carried out at a temperature of −80° to +50° C., and the concentration of the isophorone in the solvent is between 2 and 100 percent.

13. Composition consisting essentially of isophorone, ozone, an alcohol, an acid and a solvent, the alcohol being methanol, ethanol, pentanol, hexanol, butanol, isopropanol or propanol, the solvent being a hydrocarbon, a halogenated hydrocarbon, an ester solvent or an alcohol having 1 to 6 carbon atoms, and the acid being sulfuric acid, hydrochloric acid or an acid ion changer.

14. Composition as claimed in claim 13 wherein the ester solvent is acetic acid, the hydrocarbon is hexane or pentane the halogenated hydrocarbon is dichloroethane, trichloroethane, difluorobutane, dibromoethane or dichloropentane, and the alcohol is methanol or ethanol.

15. Composition consisting of 3,3-dimethyl-5-oxohexanoic acid ester, 1.2 L to 1.5 equivalents of an alkali alcoholate, and ethanol or methanol, the alkali alcoholate having an alcohol residue which has 1 to 4 carbon atoms, and the ester portion of said hexanoic acid ester having 1 to 6 carbon atoms.

16. Composition as claimed in claim 14 wherein the alkali alcoholate is sodium ethylate, sodium methylate, potassium propylate, lithium, butylate, potassium ehylate or potassium methylate.

* * * * *